(12) United States Patent
Bedingham et al.

(10) Patent No.: US 6,627,159 B1
(45) Date of Patent: Sep. 30, 2003

(54) CENTRIFUGAL FILLING OF SAMPLE PROCESSING DEVICES

(75) Inventors: William Bedingham, Woodbury, MN (US); Joel R. Dufresne, St. Paul, MN (US); Michael R. Harms, Mendota Heights, MN (US); Richard R. Matner, White Bear Lake, MN (US); Diane North, Inver Grove Heights, MN (US); Kenneth B. Wood, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 212 days.

(21) Appl. No.: 09/710,184

(22) Filed: Nov. 10, 2000

Related U.S. Application Data

(60) Provisional application No. 60/214,508, filed on Jun. 28, 2000.

(51) Int. Cl.[7] .............................. B01L 3/00; B01L 3/02; B01L 21/00; G01N 1/10
(52) U.S. Cl. .......................... 422/100; 422/99; 422/58; 422/57; 422/102; 436/180
(58) Field of Search ................................. 422/102, 100, 422/57, 58, 99; 436/180

(56) References Cited

U.S. PATENT DOCUMENTS

| | | | |
|---|---|---|---|
| 3,856,470 A | | 12/1974 | Cullis et al. |
| 4,390,499 A | | 6/1983 | Curtis et al. .................. 422/72 |
| 4,632,908 A | | 12/1986 | Schultz |
| 4,673,657 A | | 6/1987 | Christian |
| 4,806,316 A | * | 2/1989 | Johnson et al. ............. 422/100 |
| 5,154,888 A | * | 10/1992 | Zander et al. ............... 206/219 |
| 5,219,526 A | * | 6/1993 | Long ........................... 422/102 |
| 5,248,479 A | * | 9/1993 | Parsons et al. ............. 422/100 |
| 5,258,163 A | * | 11/1993 | Krause et al. ................ 422/56 |
| 5,288,463 A | * | 2/1994 | Chemelli .................... 422/102 |
| 5,310,523 A | * | 5/1994 | Smethers et al. ........... 422/102 |

(List continued on next page.)

FOREIGN PATENT DOCUMENTS

| | | | |
|---|---|---|---|
| EP | 0 169 306 | 1/1986 | |
| EP | 0 402 994 A2 | 12/1990 | |
| EP | 0 693 560 A2 | 1/1996 | |
| WO | WO 94/26414 | 11/1994 | ............. B01L/3/00 |
| WO | WO 94/29400 | 12/1994 | |
| WO | WO 95/18676 | 7/1995 | |
| WO | WO 96/15576 A1 | 5/1996 | |
| WO | WO 96/35458 | 11/1996 | |
| WO | WO 96/41864 | 12/1996 | |
| WO | WO 97/21090 | 6/1997 | |

(List continued on next page.)

OTHER PUBLICATIONS

Unger et al., "Monolithic Microfabricated Valves and Pumps by Multilayer Soft Lithography," Science vol. 288, Apr. 7, 2000, pps.113–116 XP002192277.

*Primary Examiner*—Jill Warden
*Assistant Examiner*—Brian R Gordon
(74) *Attorney, Agent, or Firm*—Christopher D. Gram; Robert W. Sprague

(57) ABSTRACT

The present invention provides methods and devices for distributing sample material to a plurality of process chambers in a sample processing device by rotating the device about an axis of rotation. The process chambers are located along conduits extending from a loading chamber and, together, the loading chamber, conduits, and process chambers form process arrays that are aligned along a length of the sample processing devices. The process arrays are unvented, i.e., access to the interior volume of the process arrays is available only through the loading chamber. Also disclosed are methods of centrifugally loading sample material into the process chambers, as well as an assembly including a sample processing device and a carrier.

18 Claims, 11 Drawing Sheets

U.S. PATENT DOCUMENTS

| | | | |
|---|---|---|---|
| 5,422,271 A | * 6/1995 | Chen et al. | 206/223 |
| 5,461,134 A | 10/1995 | Leir et al. | |
| 5,587,128 A | * 12/1996 | Wilding et al. | 216/2 |
| 5,643,738 A | 7/1997 | Zanzucchi et al. | 435/6 |
| 5,726,026 A | * 3/1998 | Wilding et al. | 422/50 |
| 5,811,296 A | * 9/1998 | Chemelli et al. | 206/223 |
| 5,833,923 A | * 11/1998 | McClintock et al. | 422/52 |
| 5,863,502 A | 1/1999 | Southgate et al. | 422/58 |
| 5,876,675 A | * 3/1999 | Kennedy | 204/451 |
| 6,007,914 A | 12/1999 | Joseph et al. | |
| 6,013,513 A | 1/2000 | Reber et al. | |
| 6,030,581 A | 2/2000 | Virtanen | |
| 6,063,589 A | 5/2000 | Kellogg et al. | |
| 6,143,248 A | 11/2000 | Kellogg et al. | |
| 6,184,029 B1 | * 2/2001 | Wilding et al. | 204/193 |
| 6,399,025 B1 | * 6/2002 | Chow | 204/269 |
| 6,413,782 B1 | * 7/2002 | Parce et al. | 436/514 |

FOREIGN PATENT DOCUMENTS

| | | | |
|---|---|---|---|
| WO | WO 98/07019 | 2/1998 | |
| WO | WO 98/49340 | 11/1998 | |
| WO | WO 99/09394 | 2/1999 | |
| WO | WO 99/44740 | 9/1999 | B01L/3/00 |
| WO | WO 99/55827 | 11/1999 | |
| WO | WO 99/58245 | 11/1999 | |
| WO | WO 99/67639 | 12/1999 | |
| WO | WO 00/05582 | 2/2000 | |
| WO | WO 00/40750 | 7/2000 | |
| WO | WO 00/50172 | 8/2000 | |
| WO | WO 00/50642 | 8/2000 | |
| WO | WO 00/69560 | 11/2000 | |
| WO | WO 00/78455 | 12/2000 | |
| WO | WO 00/79285 | 12/2000 | |
| WO | WO 01/07892 A1 | 2/2001 | |

* cited by examiner

CENTRIFUGAL FILLING OF SAMPLE PROCESSING DEVICES

CROSS REFERENCE TO RELATED APPLICATIONS

This application claims the benefit of U.S. Provisional patent application Serial No. 60/214,508 filed on Jun. 28, 2000 and titled THERMAL PROCESSING DEVICES AND METHODS, which is hereby incorporated by reference in its entirety.

FIELD OF THE INVENTION

The present invention relates to the field of sample processing devices. More particularly, the present invention relates to sample processing devices and methods of distributing sample material in sample processing devices.

BACKGROUND

Many different chemical, biochemical, and other reactions are performed on a variety of sample materials. Although it may be possible to process samples individually and obtain accurate sample-to-sample results, individual processing of samples can be time-consuming and expensive.

One approach to reducing the time and cost of processing multiple samples is to use a device including multiple chambers in which different portions of one sample or different samples can be processed simultaneously. This approach, however, presents several issues related to distribution of sample materials to the multiple chambers in the devices. Other problems may be encountered in the migration of materials between chambers during processing, which may lead to erroneous test results due to cross-chamber contamination.

SUMMARY OF THE INVENTION

The present invention provides methods and devices for distributing sample material to a plurality of process chambers in a sample processing device by rotating the device about an axis of rotation. The process chambers are located along conduits extending from a loading chamber and, together, the loading chamber, conduits, and process chambers form process arrays that are aligned along a length of the sample processing devices. The process arrays are unvented, i.e., access to the interior volume of the process arrays is available only through the loading chamber.

In other aspects, the present invention may provide sample processing devices including conduits that can be sealed by deforming one or both sides of the sample processing device to restrict or completely close off the conduit. It may be advantageous if the sample processing device includes a pressure sensitive adhesive located between two major sides of the device to assist in sealing of the conduit during and after deformation.

Other aspects of the sample processing devices may include, for example, elongated processing chambers, feeder conduits leading to the process chambers that form feeder conduit angles with the main conduit of less than 90 degrees, etc.

The process arrays in sample processing devices of the present invention may be capable of customization by selective opening and/or closing of fluid paths in the process arrays.

In some methods of centrifugal loading, it may be desirable to compress the sample processing devices during rotation to significantly reduce or eliminate leakage from the conduits and/or process chambers as a result of the centrifugal forces. Compression may be particularly helpful when used in connection with centrifugal loading of sample processing devices constructed using pressure sensitive adhesives.

The present invention also includes, in some aspects, an assembly of a carrier and a sample processing device attached to the carrier. The carrier may integral with the sample processing device, i.e., it may be provided as a single use article, or the carrier may be reusable. The carriers may advantageously include rails to support the main conduits of process arrays on the sample processing device, openings to allow for monitoring of process chambers on the sample processing devices, and other features.

In one aspect, the present invention provides a method of distributing sample material in a sample processing device by providing a sample processing device with first and second opposing ends and at least one unvented process array including a loading chamber located proximate the first end, a main conduit extending towards the second end, and a plurality of process chambers distributed along the main conduit, wherein the main conduit is in fluid communication with the loading chamber and the plurality of process chambers. The method further includes loading sample material in the loading chamber of each of the process arrays, and transporting the sample material to at least some of the process chambers by rotating the sample processing device about an axis of rotation located proximate the first end of the sample processing device, wherein the process chambers are located further from the axis of rotation than the loading chambers.

In another aspect, the present invention provides a sample processing assembly including a sample processing device with first and second opposing ends and at least one unvented process array comprising a loading chamber located proximate the first end, a main conduit extending towards the second end, and a plurality of process chambers distributed along the main conduit, wherein the main conduit is in fluid communication with the loading chamber and the plurality of process chambers; and a carrier attached to a first major side of the sample processing device, the carrier including a carrier body spaced from at least a portion of the first major side of the sample processing device.

In another aspect, the present invention provides a sample processing device including first and second opposing ends; a plurality of unvented process arrays, each of the process arrays including a loading chamber located proximate the first end; a main conduit extending towards the second end; and a plurality of process chambers distributed along the main conduit, wherein the main conduit is in fluid communication with the loading chamber and the plurality of process chambers; and wherein each of the process chambers is in fluid communication with one of the main conduits through a feeder conduit, and wherein the feeder conduits form feeder conduit angles with the main conduits that are less than 90°.

These and other features and advantages of the present invention are described below in connection with various illustrative embodiments of the devices and methods of the present invention.

DETAILED DESCRIPTION OF ILLUSTRATIVE EMBODIMENTS OF THE INVENTION

The present invention provides a sample processing device that can be used in the processing of liquid sample materials (or sample materials entrained in a liquid) in multiple process chambers to obtain desired reactions, e.g., PCR amplification, ligase chain reaction (LCR), self-sustaining sequence replication, enzyme kinetic studies, homogeneous ligand binding assays, and other chemical, biochemical, or other reactions that may, e.g., require precise and/or rapid thermal variations. More particularly, the present invention provides sample processing devices in which sample material is delivered to the process chambers by rotating the devices. The methods may also include sealing of the sample processing devices after sample material distribution.

Although various constructions of illustrative embodiments are described below, sample processing devices of the present invention may be manufactured according to the principles described in U.S. Provisional patent application Serial No. 60/214,508 filed on Jun. 28, 2000 and titled THERMAL PROCESSING DEVICES AND METHODS ;U.S. Provisional patent application Serial No. 60/214,642 filed on Jun. 28, 2000 and titled SAMPLE PROCESSING DEVICES, SYSTEMS AND METHODS; U.S. Provisional patent application Serial No. 60/237,072 filed on Oct. 2, 2000 and titled SAMPLE PROCESSING DEVICES, SYSTEMS AND METHODS.

The documents identified above all disclose a variety of different constructions of sample processing devices that could be used to manufacture sample processing devices according to the principles of the present invention. For example, although many of the sample processing devices described herein are attached using adhesives (e.g., pressure sensitive adhesives), devices of the present invention could be manufactured using heat sealing or other bonding techniques.

Figure 1:
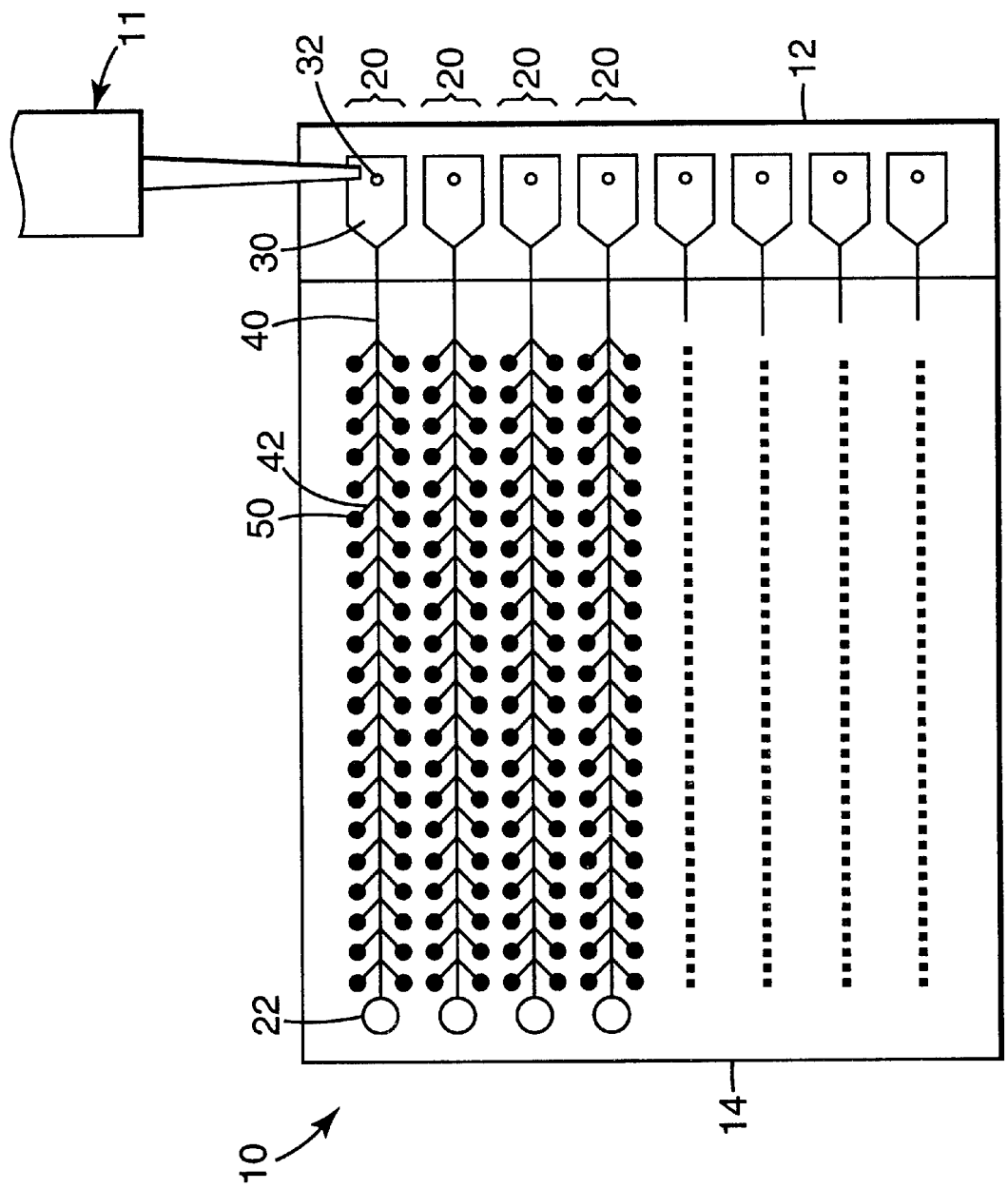
FIG. 1 is a plan view of one sample processing device.
Figure 2:
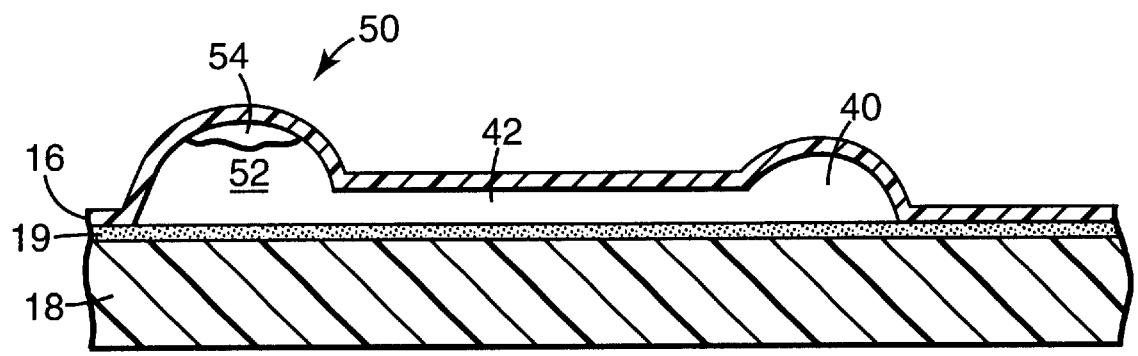
FIG. 2 is an enlarged partial cross-sectional view of one process array on a sample processing device.

One illustrative sample processing device manufactured according to the principles of the present invention is illustrated in FIGS. 1 and 2. The sample processing device 10 includes at least one, and preferably a plurality of process arrays 20. Each of the process arrays 20 extends from proximate a first end 12 towards the second end 14 of the sample processing device 10.

The process arrays 20 are depicted as being substantially parallel in their arrangement on the sample processing device 10. Although this arrangement may be preferred, it will be understood that any arrangement of process arrays 20 that results in their substantial alignment between the first and second ends 12 and 14 of the device 10 is sufficient.

Alignment of the process arrays 20 between the first and second ends 12 and 14 is important because sample materials are distributed throughout the =sample processing device by rotation about an axis of rotation proximate the first end 12 of the device 10. When so rotated, any sample material located proximate the first end 12 is driven toward the second end 14 by centrifugal forces developed during the rotation.

Each of the process arrays 20 includes at least one loading chamber 30, at least one main conduit 40, and a plurality of process chambers 50 located along each main conduit 40. It may be preferred that each of the process arrays include only one loading chamber 30 and only one main conduit 40. The process chambers 50 are in fluid communication with the main conduit 40 through feeder conduits 42. As a result, the loading chamber 30 in each of the process arrays 20 is in fluid communication with each on the process chambers 50 located along the main conduit 40 leading to the loading chamber 30. Each of the process arrays 20 depicted in FIG. 1 also includes an optional drain chamber 22 located at the end of the main conduit 40.

Each of the loading chambers 30 includes an inlet port 32 for receiving sample material into the loading chamber 30. The sample material may be delivered to port 32 by any suitable technique and/or equipment. A pipette 11 is depicted in FIG. 1, but is only one technique for loading sample material into the loading chambers 30. The pipette 11 may be operated manually or may be part of an automated sample delivery system for loading the sample material into loading chambers 30 a sample processing device 10.

Each of the process arrays 20 in the sample processing devices 10 of the present invention are preferably unvented. As used in connection with the present invention, an "unvented" process array is a process array in which the only ports leading into the volume of the process array are located in a loading chamber of the process array. In other words, to reach the process chambers within an unvented process array, sample materials must be delivered to the loading chamber through a port located in the loading chamber. Similarly, any air or other fluid located within the process array before loading with sample material must also escape from the process array through a port or ports located in the loading chamber. In contrast, a vented process array would include at least one opening outside of the loading chamber. That opening would allow for the escape of any air or other fluid located within the process array before loading during distribution of the sample material within the process array.

As seen in FIG. 2, the process chamber 50 defining a volume 52 that may include a reagent 54. It may be preferred that at least some, and preferably all, of the process chambers 50 in the devices 10 of the present invention contain at least one reagent before any sample material is distributed. The reagent 54 may be fixed within the process chamber 50 as depicted in FIG. 2. The reagent 54 is optional, i.e., sample processing devices 10 of the present invention may or may not include any reagents 54 in the process chambers 50. In another variation, some of the process chambers 50 may include a reagent 54, while others do not. In yet another variation, different process chambers 50 may contain different reagents.

Other features depicted in the sample processing device 10 are a first major side 16 and a second major side 18, between which the volume 52 of process chamber 50 is formed. Also depicted in FIG. 2 is a portion of feeder conduit 42 used to deliver sample material to the process chamber 50. The major sides 16 and 18 of the device 10 may be manufactured of any suitable material or materials. Examples of suitable materials include polymeric materials (e.g., polypropylene, polyester, polycarbonate, polyethylene, etc.), metals (e.g., metal foils), etc.

It may be preferred that at least one of the first and second major sides 16 and 18 be constructed of a material or materials that substantially transmit electromagnetic energy of selected wavelengths. For example, it may be preferred that one of the first and second major sides 16 and 18 be constructed of a material that allows for visual or machine monitoring of fluorescence or color changes within the process chambers 50.

It may also be preferred that at least one of the first and second major sides 16 and 18 be in the form of a metallic foil. The metallic foil may include a passivation layer on the surfaces that face the interiors of the loading chambers 30, main conduits 40, feeder conduits 42, and/or process chambers 50 to prevent contamination of the sample materials.

In the illustrative embodiment of the sample processing device depicted in FIGS. 1 and 2, the first major side 16 is preferably manufactured of a polymeric film (e.g., polypropylene) that is formed to provide structures such as the loading chambers 30, main conduit 40, feeder conduits 42, and process chambers 50. The second major side 18 is preferably manufactured of a metallic foil, e.g., an aluminum or other metal foil. The metallic foil is preferably deformable as discussed in more detail below.

The first and second major sides 16 and 18 may be attached by any suitable technique or techniques, e.g., heat sealing, ultrasonic welding, etc. It may, however, be preferred that the first and second major sides 16 and 18 be attached using adhesive. As depicted in FIG. 2, the adhesive may preferably be provided in the form of a layer of adhesive 19. It may be preferred that the adhesive layer 19 be provided as a continuous, unbroken layer over the surface of at least one of the first and second major sides 16 and 18. It may, for example, be preferred that the adhesive layer 19 be provided on the metallic foil of major side 18.

A variety of adhesives may be used, although any adhesive selected should be capable of withstanding the forces generated during processing of any sample materials located in the process chambers 50. Those forces may be large where, e.g., the processing involves thermal cycling as in, e.g., polymerase chain reaction and similar processes. The adhesives may include, e.g., hot melt adhesives, curable adhesives, pressure sensitive adhesives, etc.

Among the pressure sensitive adhesives that may be used in connection with the sample processing devices of the present invention are those that are resistant to high temperatures and humidity. It may, for example, be preferred to use silicone pressure sensitive adhesives. Examples of some suitable siliconebased pressure sensitive adhesives are silicone-polyurea compositions as described in, e.g., U.S. Pat. Nos. 5,461,134 and 6,007,914 or International Publication No. WO 96/35458 that contain a sufficient level of tackifying resin to provide the desired tackiness to the composition.

It may be preferred that all features, e.g., loading chambers 30, main conduit 40, feeder conduit 42, process chambers 50, and drain chambers 22, be formed in the first major side 16 while the second major side 18 is substantially flat. By locating all of the features in one side of the sample processing device 10, the need for aligning the two sides together before attaching them may be eliminated. Furthermore, a flat second major side 18 may promote intimate contact with, e.g., a thermal block such as that used in thermal cycling equipment. Alternatively, however, it will be understood that features may be formed in both sides 16 and 18 of sample processing devices according to the present invention.

Figure 3:
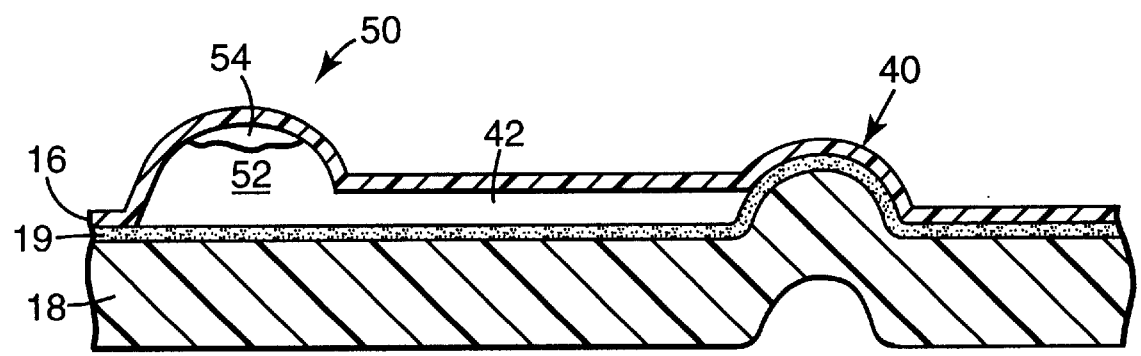
FIG. 3 is an enlarged partial cross-sectional view of the process array of FIG. 2 depicting one method of sealing the main conduit.

Another potential feature of the sample processing devices of the invention is isolation of the process chambers 50 by closing the fluid pathways in the devices 10. Referring now to FIGS. 2 and 3, the process chambers 50 may be isolated after distribution of any sample materials by deforming the second major side 18 such that it extends into one or both of the main conduits 40 or the feeder conduits 42 in each of the process arrays 20. FIG. 3 illustrates one such closure method where the second major side 18 is deformed into the main conduit 40, with the adhesive layer 19 located between the two sides.

The desire to hermetically seal fluid pathways in the sample processing devices 10 of the present invention may lead towards the use of pressure sensitive adhesive for the adhesive layer 19. Where a pressure sensitive adhesive is present between the first and second major sides 16 and 18 of the device, deformation of the second major side 18 may result in adhesion between the first and second major sides 16 and 18 in the deformed area. That adhesion may enhance any sealing or closure produced by the deformation. The need for hermetic sealing may be more acute when the sample processing devices are to be used in thermal processing reactions such as, e.g., polymerase chain reaction, in which any liquids in the devices can exert high pressures on the seals due to thermal expansion.

After distribution of sample materials into the process chambers 50 is completed, it may be desirable to isolate the process chambers 50 from each other. Isolation may be accomplished in a variety of manners. For example, isolation of the process chambers 50 may involve deformation of the feeder conduits 42 and/or main conduits 40 within each of the process arrays 20.

For those sample processing devices that include a metallic layer, isolation of the process chambers 50 may involve plastic deformation of the metallic layer to close the main conduits 40 and/or feeder conduits 42. If, for example, a pressure sensitive adhesive 19 is used to attach the first and second major sides 16 and 18 of the sample processing device together, that same pressure sensitive adhesive may improve the sealing of main conduits 40 and/or feeder conduits 42 by adhering the deformed first and second major sides 16 and 18 together.

It should be understood, however, that complete sealing of the deformed portions of the sample processing device 10 may not be required. For example, it may only be required that the deformation restrict flow, migration or diffusion through a conduit or other fluid pathway sufficiently to provide the desired isolation.

In one method in which the process arrays 20 are closed after distribution of sample materials into process chambers 50, it may be necessary to deform only a portion of the main conduit 40 or, alternatively, the entire length of the distribution channel 40. Where only a portion of the main conduit 40 is deformed, it may be preferred to deform that portion of the main conduit 40 located proximate the loading chamber 30.

Sealing all of the main conduit 40 by forcing the sides 16 and 18 together along the length of the conduit 40 may provide advantages such as driving any fluid located in the main conduit 40 back into the loading chamber 30. One potential advantage, however, of sealing only a portion of the main conduit 40 is that either none or only a small amount of any fluid material located in the main conduit 40 would be returned to the loading chamber 30.

Figure 4:
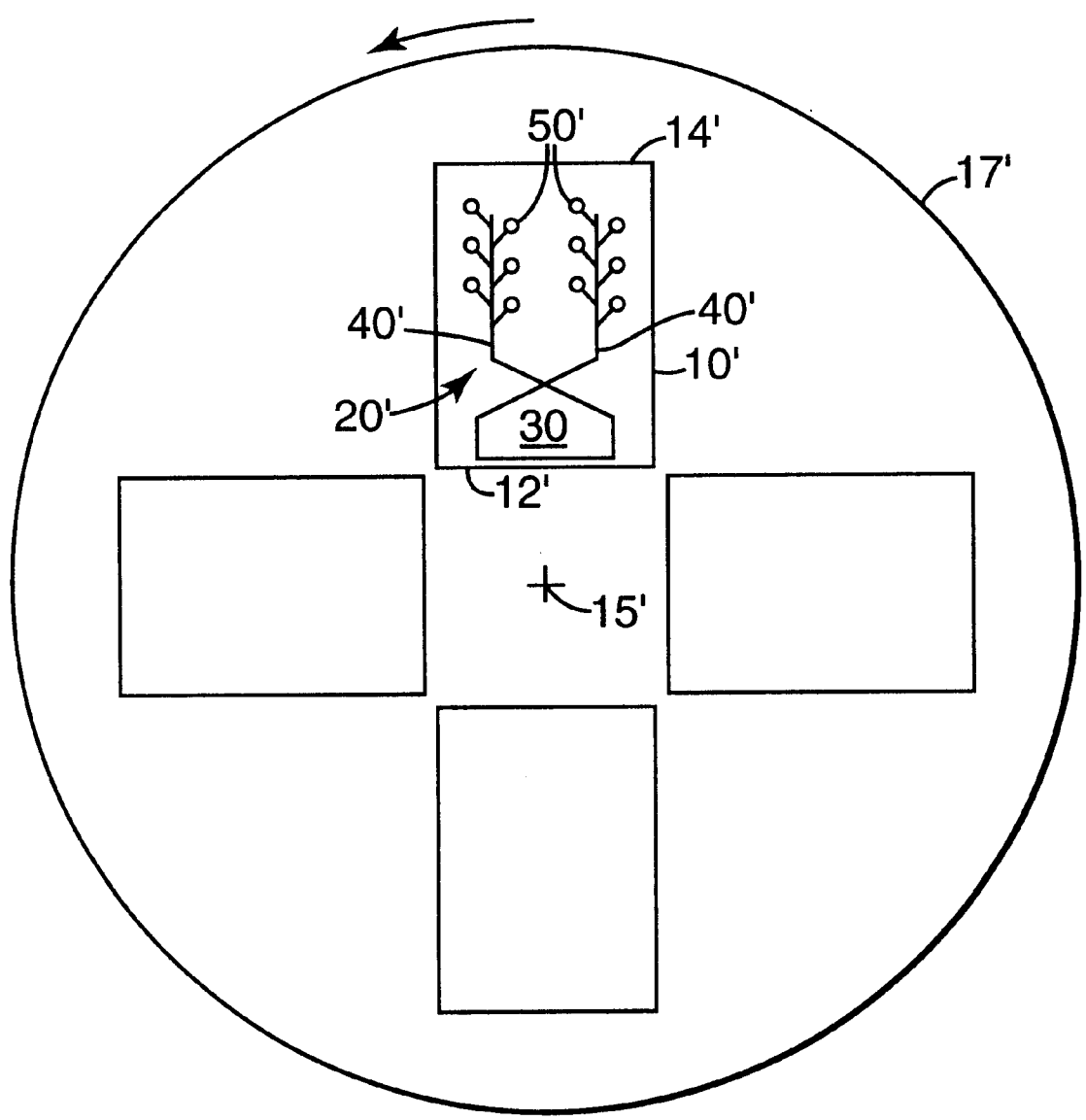
FIG. 4 is a plan view of one centrifuge system for rotating sample processing devices.

Methods of distributing sample materials by rotating a sample processing device according to the present invention will now be described with reference to FIG. 4. After providing a sample processing device 10' that includes first and second opposing ends 12' and 14' with at least one process array 20' aligned between the ends 12' and 14' of the device 10', sample material may be delivered to the process chambers 50' of the process array 20' by rotating. It should be noted that the sample processing device 10' includes only one process array 20' with a single loading chamber 30' connected to the process chambers 50' along two main conduits 40'.

The amount of sample material delivered to each of the loading chambers on the devices 10' may vary. It may, however, be preferred that the volume of sample material delivered to each of the loading chambers is no greater than the combined volumes of any main conduits, feeder conduits, and process chambers in fluid communication with the loading chamber. Where an optional drain chamber (see, e.g., FIG. 1) is located at the distal and of the process array, the amount of sample material delivery to each of the loading chambers may be increased to compensate for the additional volume of the process array downstream from the loading chamber.

After the loading chambers contain the desired sample material, that sample material must be transported to the process chambers within each of the process arrays. Referring to FIG. 4, the distribution of sample material is effected by rotating the sample processing device 10' about an axis of rotation 15' located proximate the first end 12' of the sample processing device 10'. Rotation of the device 10' about the axis of rotation 15' when so oriented will result in centrifugal forces on any sample materials located within the loading chamber 30'. The centrifugal forces will drive the sample material out of the loading chamber 30' and into the main conduits 40' for delivery to the process chambers 50'.

The sample processing device 10' is oriented such that the process chambers 50' are located further from the axis of rotation 15' than the loading chamber 30'. The sample processing device 10' is located on a platter 17' that rotates about the axis 15'. The platter 17' may preferably be capable of accepting more than one sample processing device 10' for simultaneous rotation about axis 15'.

The orientation of the sample processing devices relative to the axis of rotation 15' is not critical, provided that the process chambers are located further from the axis of rotation 15' than the loading chambers. For example, where the sample processing device 10' is in the form of a substantially flat card-like article, the edge of the first end 12' of the sample processing device 10' may be oriented substantially perpendicular to the axis of rotation as depicted in FIG. 4. Alternatively, the axis of rotation 15' may be substantially aligned with (e.g., parallel to) the edge of the first end 12' of the sample processing device 10. A multitude of orientations of the first end 12' relative to the axis 15' can be envisioned between parallel and perpendicular, all of which are acceptable as long as the process chambers are distal from the axis 15' relative to the loading chambers on the devices.

Because the process arrays of sample processing devices according to the present invention are preferably unvented as described above, distribution of sample materials to the process chambers may be difficult due to the air or other fluids trapped within the process chambers. Among the techniques that may be used to assist in distribution of the sample materials are selection of the materials used to construct the sample processing device, the addition of materials to the sample material (e.g., the addition of a surfactant to reduce surface tension in the sample material), manipulation of the viscosity of the sample material (e.g., by heating), etc.

One advantage of centrifugal loading of sample materials into process chambers is the ability to rotate the sample processing device and inspect the device after an initial period of rotation to determine whether sample material has been adequately distributed to the process chambers. If distribution is not satisfactory, the sample processing device can be rotated again until satisfactory sample material distribution is obtained.

In addition to, or in place of, a sequential rotate-inspect-rotate approach, the methods of the present invention may also employ two or more acceleration/deceleration cycles to assist in distribution of sample materials from the loading chambers to the process chambers. Alternating acceleration and deceleration of the device during rotation may essentially burp the sample materials through main conduit and feeder conduits (if any) into process chambers. It may also be helpful if the acceleration and/or deceleration are rapid. The rotation may also preferably only be in one direction or it may be in opposite directions.

The actual acceleration and deceleration rates may vary based on a variety of factors such as temperature, size of the sample processing device, size of the conduits and chambers, distance of the sample material from the axis of rotation, materials used to manufacture the devices, properties of the sample materials (e.g., viscosity), etc. one example of a useful acceleration/deceleration cycle may include an initial acceleration to about 4000 revolutions per minute (rpm), followed by deceleration to about 1000 rpm over period of about 1 second, with oscillations in rotational speed of the device between 1000 rpm and 4000 rpm at 1 second intervals until a sample materials are distributed.

In addition to constant speed rotation and acceleration/deceleration cycling during rotation, the methods of the present invention may also include vibration of the sample processing device to assist in the distribution of sample materials into process chambers. Vibration, such as tapping, high frequency oscillations, etc., may assist in removal of entrapped air bubbles located within the conduits or process chambers. Vibration of the sample processing device may be employed before or after rotation, or it may be employed during rotation of the sample processing device about the axis of rotation.

Figure 5:
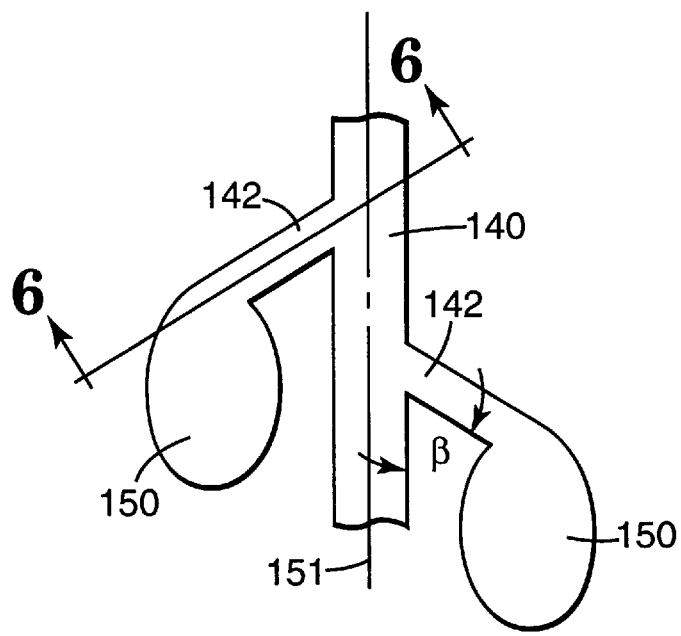
FIG. 5 is a plan view of a portion of an alternative process array.

Although the process chambers illustrated in device 10 of FIG. 1 appear substantially circular in shape, it should be understood that the process chambers used in sample processing devices of the present invention may take any suitable shape. One example of an alternative shape is depicted in FIG. 5 in which the process chambers 150 are in the form of oval shapes that are elongated along axis 151. The axis 151 is preferably generally aligned with the main conduit 140. As a result, the axis 151 will generally extend from the first end of the sample processing device to its second end, with the oval shapes of process chambers 150 having their largest dimension aligned between the first and second ends of the sample processing device.

FIG. 5 also depicts feeder conduits 142 that are preferably angled off of the main conduit 140 and adjoin the process chambers 150 at one end. It may be further preferred that the feeder conduits 142 meet the process chambers 150 at the end closest to the first end of the sample processing device (which is, therefore, the end of the process chamber that is closest to the axis of rotation during loading). Entry of the feeder conduits 142 into the process chambers 150 at the end may facilitate removal of air within the chambers 150 during loading.

The feeder conduit angle B, i.e., the included angle formed between the feeder conduits 142 and the main conduit 140, may also enhance filling of the process chambers 150 by promoting the removal of the air. It may, for example, be preferred that the feeder conduit angle be less than 90 degrees, more preferably less than 75 degrees. The feeder conduit angle will always be measured between the side of the feeder conduit 142 facing away from the first end of the device and the main conduit 140.

Another potentially advantageous optional feature illustrated in FIG. 5 is the longitudinal offset of the feeder conduits 142 on opposing sides of the main conduit 140 (as opposed to the cross-conduit alignment of the feeder conduits 42 in FIG. 1). That offset between the points at which the opposing feeder conduits 142 join the main conduit 140 may assist in preventing cross-chamber contamination during filling and/or processing.

Figure 6:
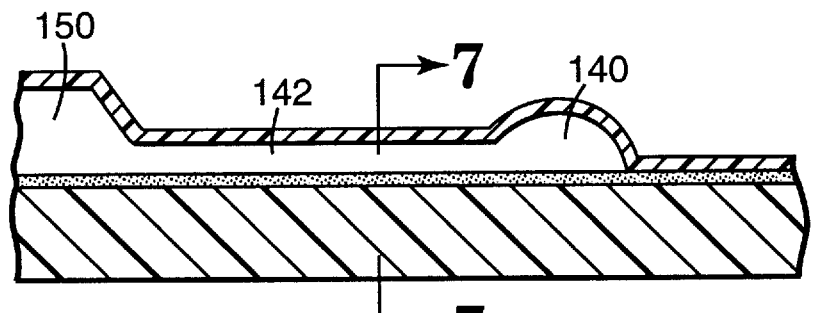
FIG. 6 is a cross-sectional view taken along line 6—6 in FIG. 5.
Figure 7:
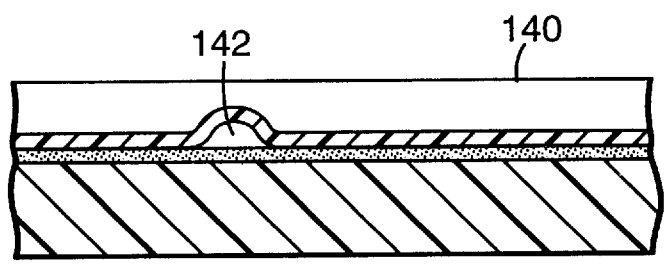
FIG. 7 is a cross-sectional view taken along line 7—7 in FIG. 6.

FIGS. 6 and 7, in conjunction with FIG. 5, illustrate yet another optional feature of the sample processing devices of the present invention. FIG. 6 is a cross-sectional view of FIG. 5 taken along line 6—6 in FIG. 5 and FIG. 7 is a cross-sectional view of FIG. 6 taken along line 7—7 in FIG. 6. The figures illustrate the smaller cross-sectional area of the feeder conduit 142 as compared to the main conduit 140. The different cross-sectional area of the conduits 140 and 142 is achieved, in the illustrated embodiment, by different heights and widths in the two conduits. Providing conduits with different cross-sectional areas may limit diffusion of sample material from the process chambers 150 into the main conduit 140 after and/or during filling. By limiting diffusion, cross-chamber contamination may also be reduced.

Figure 8:
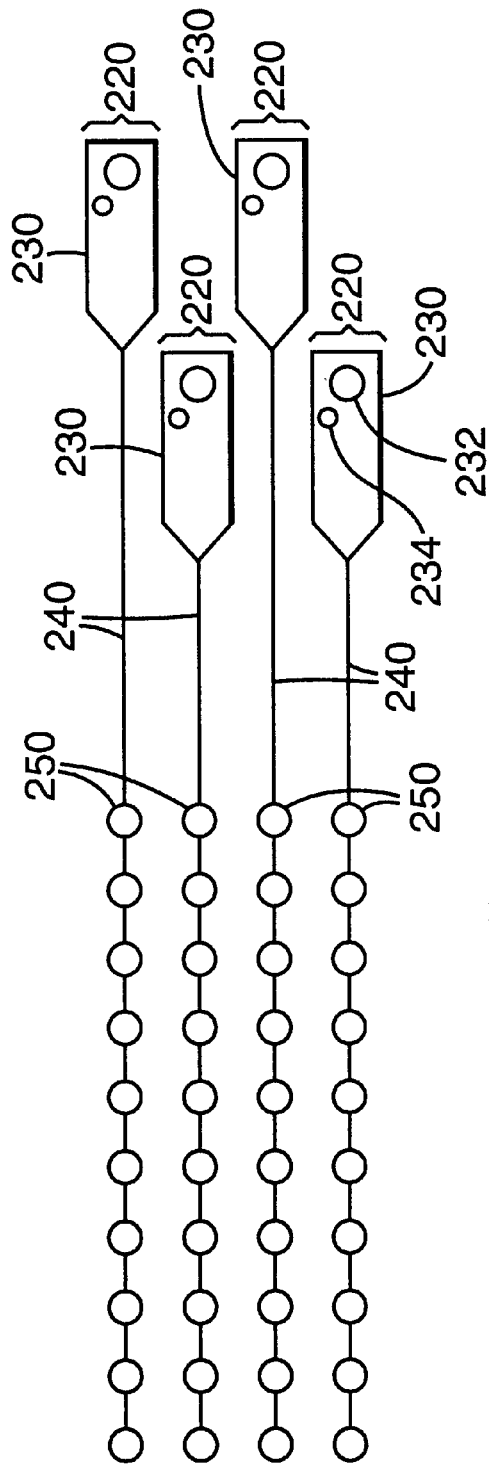
FIG. 8 depicts an alternative set of process arrays for a sample processing device.

FIG. 8 is a schematic diagram illustrating another arrangement for process arrays 220 useful in sample processing devices of the invention. Among the features depicted in connection with process arrays 220 are the staggered relationship between loading chambers 230. Such a staggered relationship may improve the density or spacing between process chambers 250.

Each of the loading chambers 230 also includes a loading port 232 and a vent port 234 which may facilitate rapid filling of the loading chambers 230 by providing a pathway separate from the loading port 232 for air to escape during filling of the loading chamber 230.

Another feature depicted in FIG. 8 is the serial relationship between the process chambers 250 located along each of the main conduits 240. Each pair of successive process chambers 250 is in fluid communication with each other along main conduit 240. As a result, if any reagents or other materials are to be located within process chambers 250 before distribution of the sample material, then some mechanism or technique for preventing removal of those materials during distribution of the sample material must be provided. For example, the reagents may be contained in a wax or other substance within each of the process chambers 250.

Figure 9:
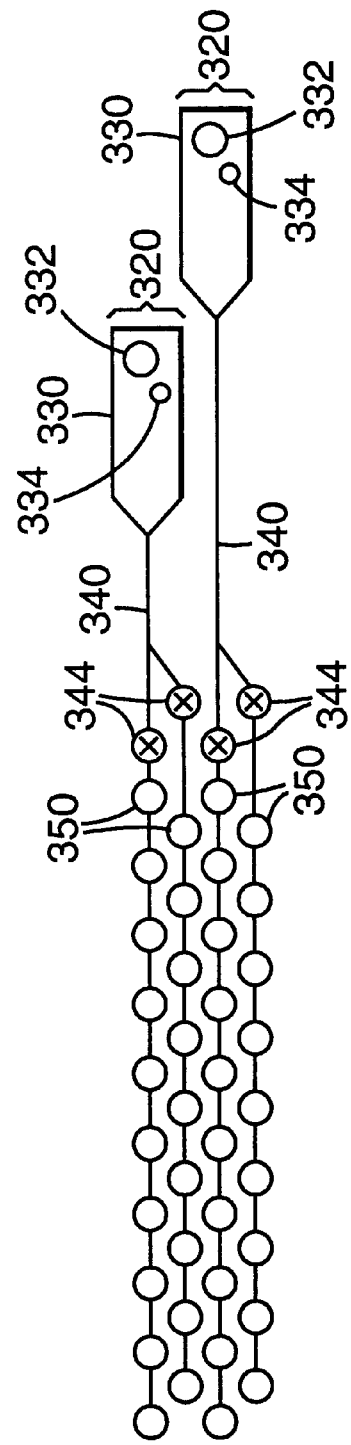
FIG. 9 depicts an alternative set of process arrays for a sample processing device.

FIG. 9 is a schematic diagram illustrating yet another arrangement of process arrays 320 that may be used in connection with sample processing devices of the present invention. Each of the process arrays 320 includes a loading chamber 330 that, in turn, includes a loading port 332 and a vent port 334. The loading chambers 330 are in fluid communication with a plurality of process chambers 350 through main conduits 340.

One feature illustrated in connection with FIG. 9 is the addition of valves 344 along the main conduits 340. Each of the main conduits 340 bifurcates to an individual subset of process chambers 350. By selectively opening or closing the valves 344 (which may be either closed or open when manufactured) the delivery of sample material to each subset of process chambers 350 may be enabled or prevented. For example, if one of the valves 344 is open while the other valve 344 is closed, delivery of sample material will be effected only to one subset of process chambers 350 (through the open valve 344).

It may be possible to achieve the same result, i.e., enabling or preventing delivery of sample material to a subset of process chambers 350, by sealing the main conduit 340 at an appropriate location after the bifurcation point. The use of valves 344 may, however, provided the ability for automated control or customization of the sample processing device including process arrays 320. The valves 344 may take any suitable form, some examples of which are described in the patent applications identified above.

By using customizable process arrays 320, it may be possible to provide sample processing devices that are tailored at the point of use for particular testing needs. Other advantages may be found in the ability to reduce the volume of sample material needed by reducing the number of process chambers 350 to which that sample material may be delivered. Alternatively, where a higher level of confidence is required, the valves 344 may be opened to increase the number of process chambers 350 to which sample material is delivered, thereby increasing the number of tests performed.

Figure 10:
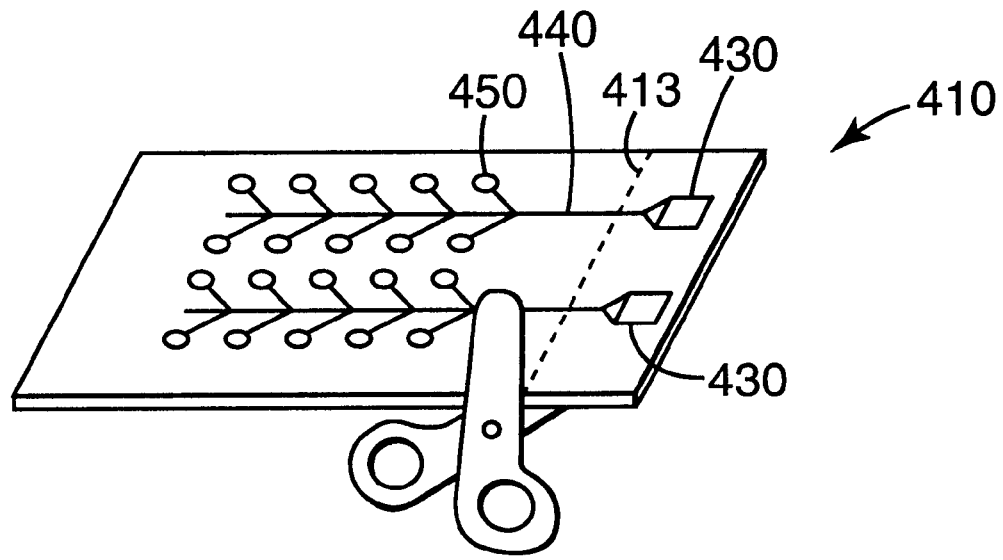
FIG. 10 is a perspective view of a sample processing device in which the loading chambers are being separated from the remainder of the sample processing device.

Referring now to FIG. 10, another optional feature of the present invention is separation of the loading chambers 430 from the remainder of the sample processing device 410. Separation of the loading portion of the sample processing device 410 from the portion containing the process chambers 450 may provide advantages such as, for example, reducing the size of the sample processing device 410, reducing the thermal mass of the sample processing device 410, removing any sample materials that may remain within the loading chambers 430 after distribution to process chambers 450, etc.

Separation of the loading chambers 430 from the sample processing device 410 may involve, for example, cutting the sample processing device 410 along the separation line 413 as depicted in FIG. 10. Where the loading chambers 430 are to be physically separated from the remainder of the sample processing device 410, it is typically preferable that the main conduits 440 be sealed across at least the separation line 413 to prevent leakage of the sample materials during and after the separation process.

The use of a pressure sensitive adhesive within the main conduits 440 (see, e.g., FIGS. 2 and 3) may be particularly helpful to ensure adequate sealing of the main conduits. In addition to, or in place of, pressure sensitive adhesives within the conduits 440, it may be desirable to further seal the main conduits 440 by, e.g., the application of heat and/or pressure to bond the conduit closed.

Figure 11:
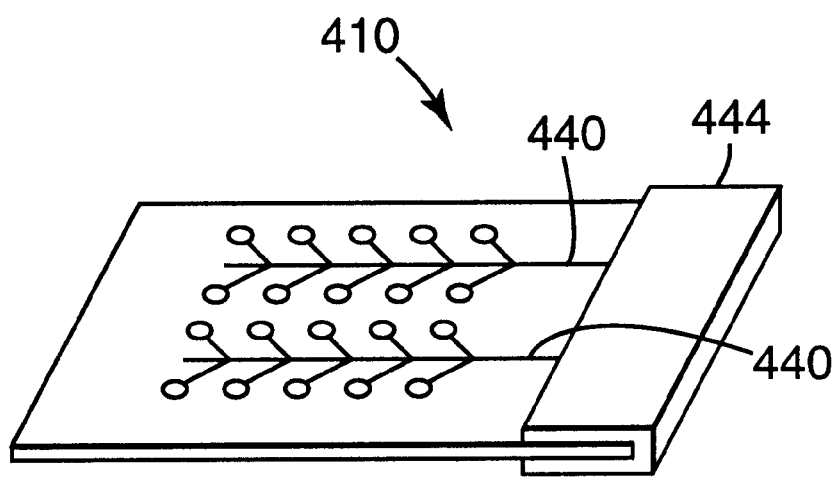
FIG. 11 is a perspective view of the sample processing device of FIG. 10 after sealing.

If additional sealing is required, it may also be helpful to cover the ends of the main conduits with a seal 444 as illustrated in FIG. 11. The seal may be provided, e.g., in the form of an adhesive coated foil or other material. Alternatively or in addition to the use of an adhesive to secure the seal 444, it may be desirable to, e.g., heat seal the seal 444 in place on the sample processing device 410.

Figure 12:
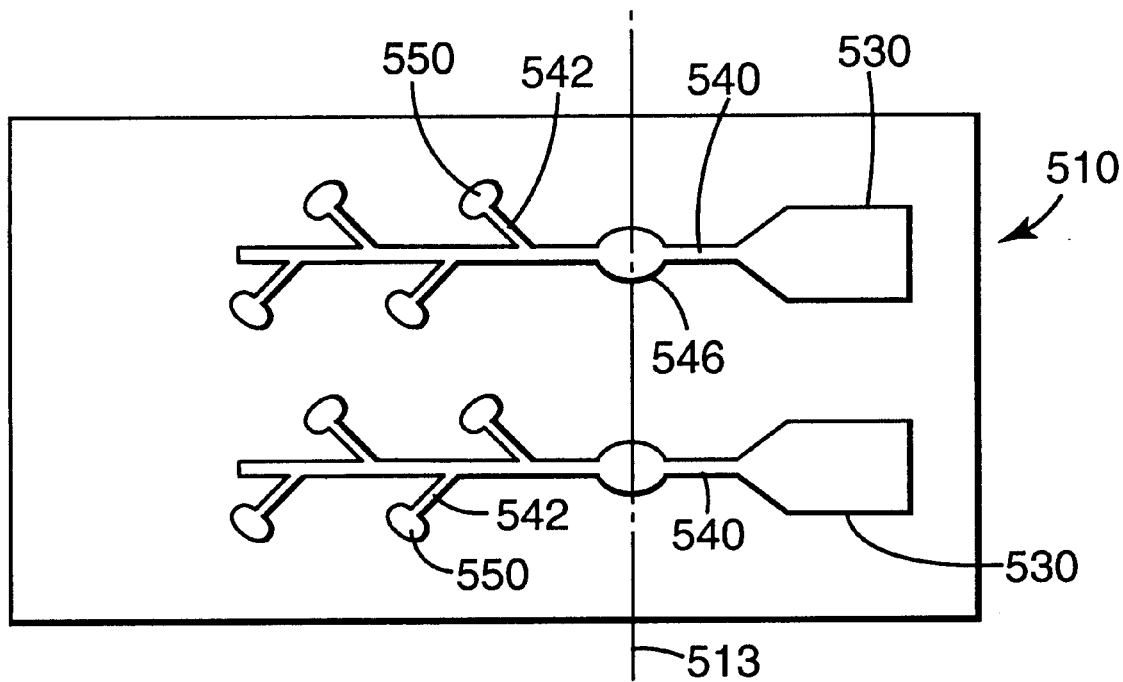
FIG. 12 is a plan view of another sample processing device.
Figure 13:
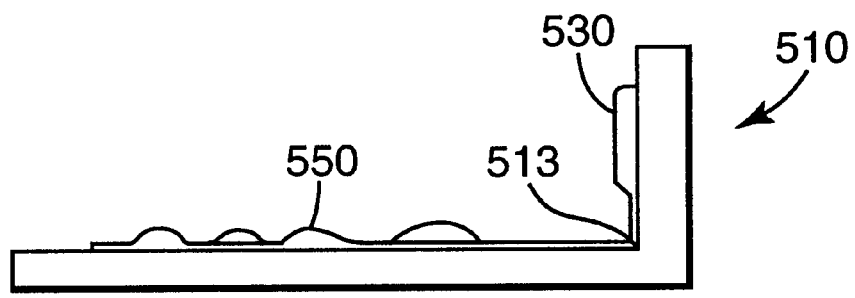
FIG. 13 is a side view of the sample processing device of FIG. 12 after folding the device along a line separating the loading chambers from the process chambers.

Referring now to FIGS. 12 and 13, one alternative to physical separation of the loading chambers 530 from the remainder of the sample processing device 510 may include folding the sample processing device 510 along, e.g., separation line 513. That folding process may also close the main conduit 540 across the separation line 513 by crimping the main conduits 540, such that a desired level isolation may be achieved between the process chambers 550 without further deformation of any of the main conduits 540 or the feeder conduits 542.

It may be desirable to provide crimping areas 546 located at the intersections of the main conduits 540 with the folding line 513 that are wider and shallower than the surrounding portions of conduits 540 to facilitate crimping of the conduits 540 during folding. The wider, shallower crimping areas 546 do, however, preferably provide a cross-sectional area for fluid flow that is similar to the cross-sectional fluid flow area of the surrounding portions of the main conduits 540.

The centrifugal forces developed during rotation of the sample processing devices to deliver the sample materials to process chambers may challenge the sealing of the process chambers and other fluid pathways in each of the process arrays. The challenges may be especially acute when the sample processing device is constructed using an adhesive to attach to layers together.

Figure 14:
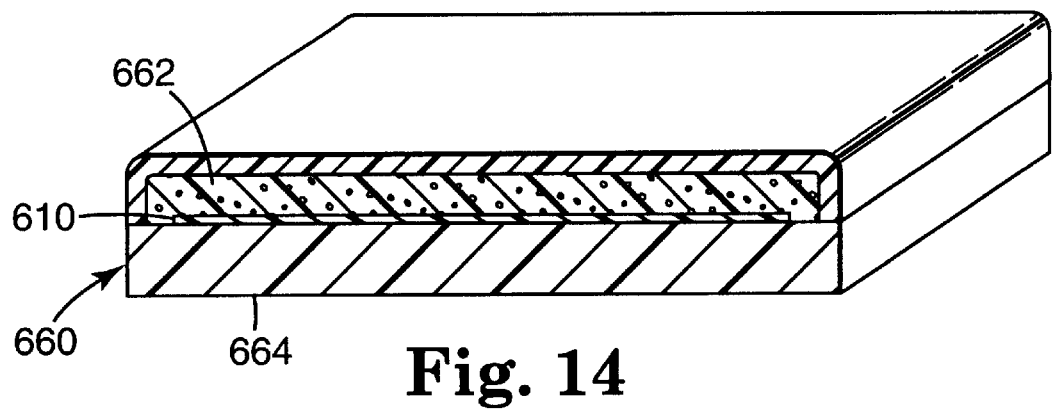
FIG. 14 depicts a sample processing device located within a compression device.

To assist with the sealing of the process chambers and other fluid pathways on the sample processing devices during rotation, it may be advantageous to compress the major sides of the sample processing devices together during rotation. Referring to FIG. 14, the sample processing device 610 may, for example, be located within a compression device 660 (e.g., in the form of a clamshell or other suitable structure) that compresses the major sides of the sample processing device 610 together during rotation. The compression device 660 may, for example, include conformable material 662 in contact with one side of the sample processing device 610. The conformable material 662 may, for example be a resilient foam or similar composition.

Also included in the compression device 660 is a base 664 in contact with the opposing side of the sample processing device 610. As the conformable material 662 and the base 664 are biased toward each other, the major sides of the sample processing device 610 are compressed. That compression may significantly reduce or prevent leakage of any sample materials out of the process chambers or other fluid pathways during rotation of the sample processing device 610.

The conformable material 662 is preferably located in contact with the side of the device 610 that includes any structures such as process chambers or conduits protruding therefrom to avoid damaging those structures. The base 664 may be formed of any suitable material which may be rigid where no structures are protruding from the side of the device 610 facing the base 664.

Figure 15:
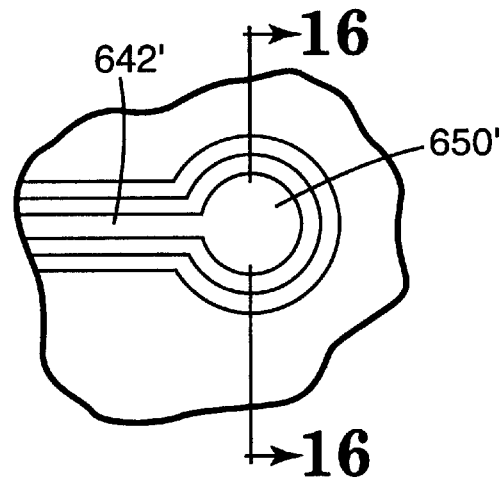
FIG. 15 is a plan view of an alternative compression device.
Figure 16:
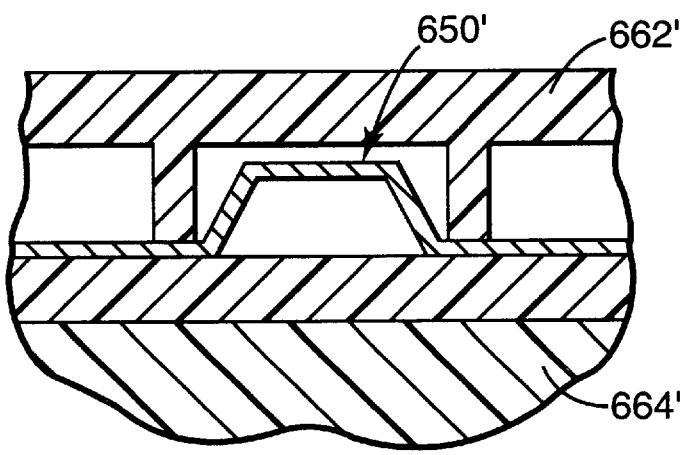
FIG. 16 is a cross-sectional view taken along line 16—16 in FIG. 15.
Figure 17:
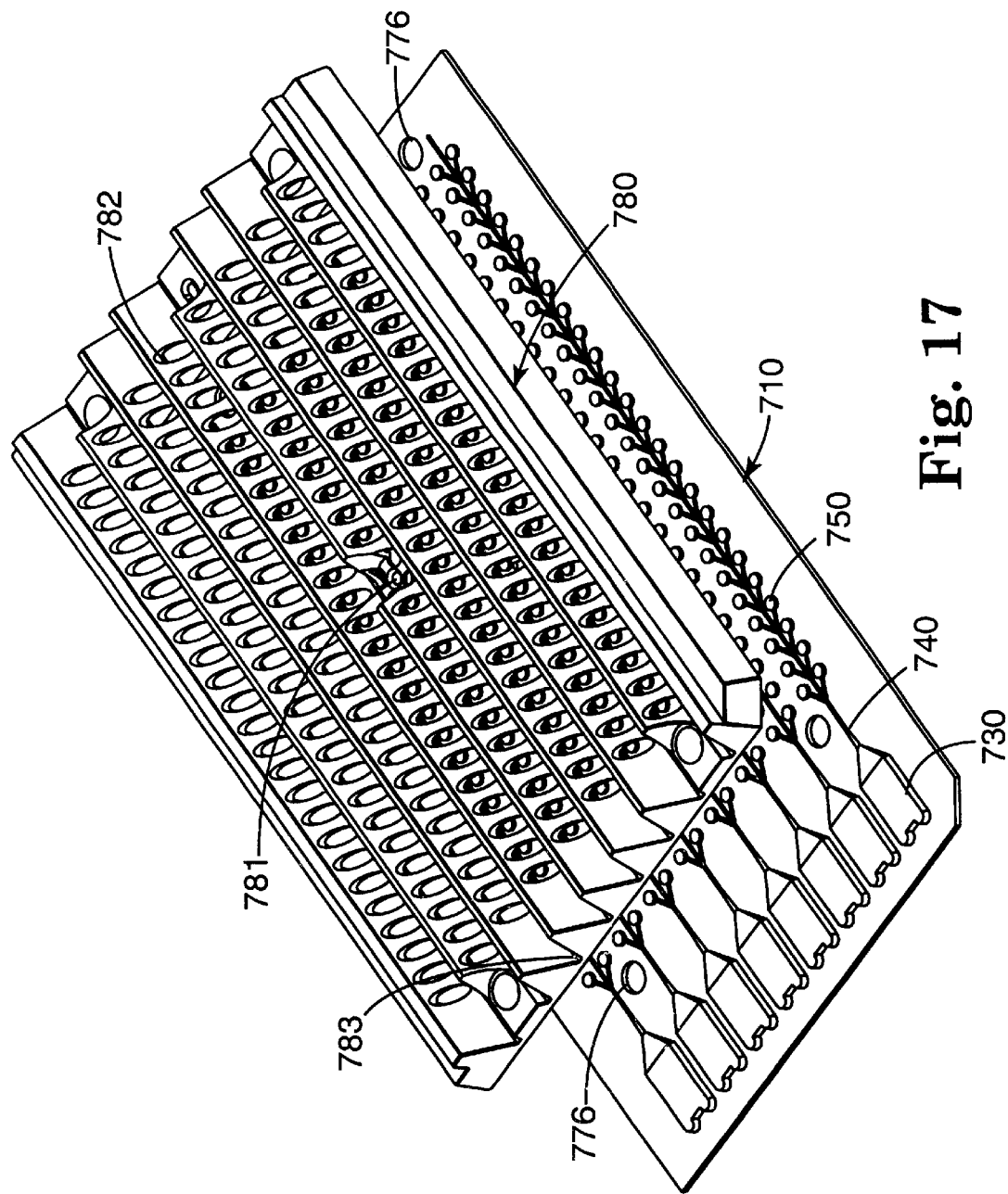
FIG. 17 is an exploded perspective view of an assembly including a sample processing device and a carrier.

A portion of an alternative compression device is depicted in FIGS. 15 and 16 in connection with a process chamber 650' and portion of a feeder conduit 642'. The alternative compression device is designed to provide pressure. The compression device includes a shaped compression die 662' that applies pressure about the periphery of the process chamber 650' and the feeder conduit 642'. The compression die 662' preferably acts against a base 664' located on the opposite side of the sample processing device. Departing from the design of the compression device depicted in FIG. 14, the compression die 662' may preferably be formed of a substantially rigid material FIG. 17 is an exploded perspective view of an assembly including a sample processing device 710 of the present invention and a carrier 780. Because, in many instances, the sample processing devices 710 are manufactured from materials that are relatively thin, it may be desirable to attach the device 710 to a carrier 780 for a variety of reasons. Among those reasons are the need to provide an assembly having sufficient thickness to be processed in existing thermal processing equipment with a minimum of modification to that equipment.

By providing a carrier 780 that is separate from the sample processing device 710, the thermal mass of the sample processing device 710 can be minimally affected as compared to manufacturing the entire sample processing device 710 with a thickness suitable for processing in conventional equipment. Another potential advantage of a carrier 780 is that the sample processing devices 710 may exhibit a tendency to curl or otherwise deviate from a planar configuration. Attaching the device 710 to a rigid carrier 780 can retain the sample processing device in a planar configuration for processing.

The carrier 780 may be attached to the sample processing device 710 in a manner that allows for the carrier 780 to be reused with many different sample processing devices 710. Alternatively, each carrier 780 may be permanently attached to a single sample processing device 710 such that, after use, both the sample processing device 710 and the carrier 780 are discarded together.

The sample processing device 710 may be manufactured as described above. The carrier 780 may include various features such as carrier openings 782 that are preferably aligned with the plurality of process chambers 750 in the device 710. By providing carrier openings 782, the process chambers 750 can be viewed from the side of the sample processing device 710 facing the carrier 780. One alternative to providing the plurality of carrier openings 782 is to manufacture the carrier 780 of a material (or materials) transmissive to electromagnetic radiation in the desired wavelengths. As a result, it may be possible to use a carrier 780 that is contiguous over the surface of the sample processing device 710, i.e., the carrier provides no openings for access to the process chambers 750.

Figure 18:
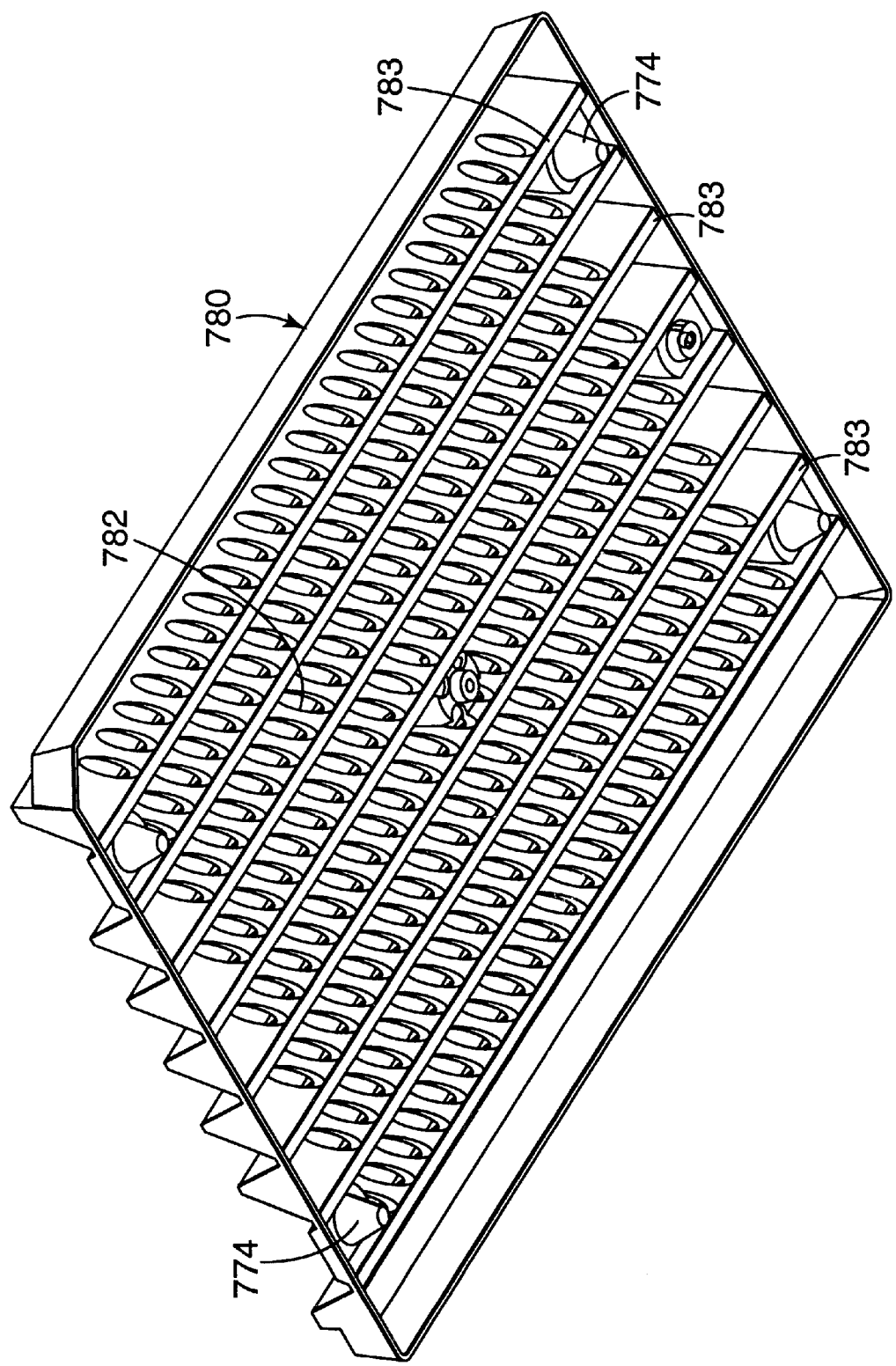
FIG. 18 is a perspective view of the carrier of FIG. 18 taken from the side of the carrier facing the sample processing device.

The carrier 780 illustrated in FIGS. 17 and 18 may also provide advantages in the sealing or isolation of the process chambers 750 after loading. FIG. 18 illustrates the rails 783 in the carrier 780 that extend along the length of the main conduits 740 in the associated sample processing device 710. The rails 783 may, for example, provide a surface against which the main conduits 740 of the sample processing device 710 may be pressed while the conduit is deformed to isolate the process chambers 750 and/or seal the conduits 740 prior to separating the loading chambers 730 from the device 710.

In addition to their use during deformation of the main conduits 740, the rails 783 may also be relied on during, e.g., thermal processing to apply pressure to the conduits 740 (thereby potentially improving the seals formed along the main conduits 740). Furthermore, the use of rails 783 also provides an additional advantage in that they provide for significantly reduced contact between the sample processing device 710 and the carrier 780 while still providing the necessary support for sealing of the main conduits 740 on device 710. The importance of reducing contact between the carrier 780 and device 710 may be particularly important when the assembly is to be used in thermal processing of sample materials (e.g., polymerase chain reaction, etc.). As such, the carrier 780 may be characterized as being spaced from the sample processing device 710 between the main conduits 740 when the rails 783 are aligned with the main conduits 740.

Various alignment features are also illustrated in FIGS. 17 and 18, including structures that align the sample processing device 710 relative to the carrier 780, as well as structures that align the assembly of sample processing device 710 and carrier 780 relative to, e.g., a thermal processing system used to thermally cycle materials in the sample process chambers 750. Alignment may also be used in connection with a detection system for detecting the presence or absence of a selected analyte in the process chambers 750.

It may be preferred that the sample processing device 710 be aligned relative to the carrier 780 proximate a center of both of those articles (center 781 of carrier 780 being indicated in FIG. 17). To prevent rotation of the sample processing device 710 relative to the carrier 780, at least two points of registration or contact are required. Because the device 710 and carrier 780 may be subjected to temperature extremes during processing, it may be desirable, for example, that the sample processing device 710 be fixedly connected to carrier 780 in the center of the two articles, while any additional points of attachment provide for differential expansion/contraction between the device 710 and carrier 780.

The alignment structures used to align the assembly as a whole to, e.g., thermal cycling and/or detection equipment, include protrusions 774 that are preferably designed to extend through alignment openings 776 in the sample processing device 710. As a result, alignment of the assembly is based on structures found in carrier 780. One advantage to relying on the carrier 780 for alignment structures is that its construction will typically being more dimensionally stable and accurate as compared to the sample processing device 710.

Figure 19:
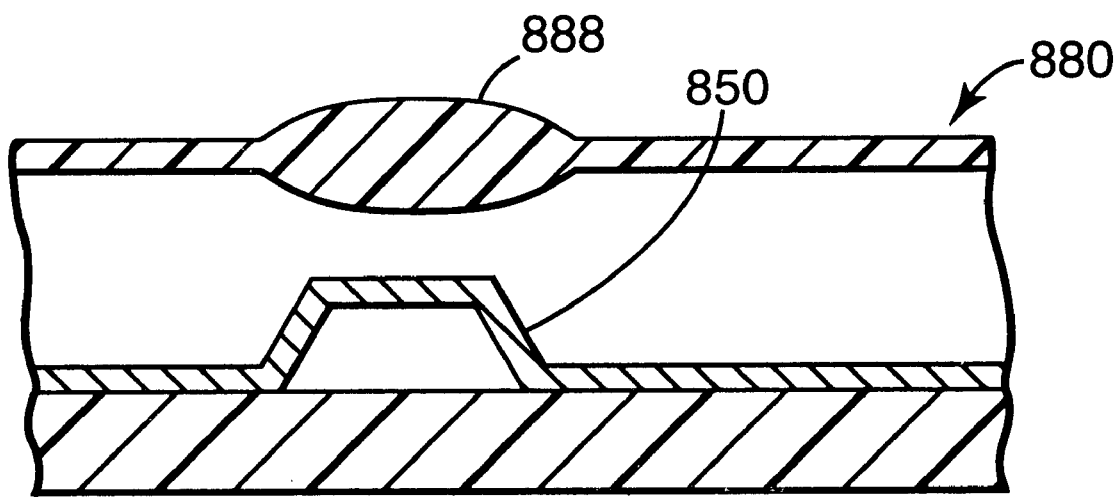
FIG. 19 is a partial cross-sectional view of a sample processing device and carrier including an optical element.

FIG. 19 illustrates yet another optional feature of carriers used in connection with the present invention. The carrier 880 is depicted with an optical element 888, e.g., a lens, that may assist in focusing electromagnetic energy directed into the process chamber 850 or emanating from the process chamber 850. The optical element 888 is depicted as integral with the carrier 880, although it should be understood that the optical element 888 may be provided as a separate article that is attached to the carrier 880.

Patents, patent applications, and publications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

What is claimed is:

1. A sample processing assembly comprising:
    a sample processing device comprising first and second opposing ends and at least one unvented process array comprising a loading chamber located proximate the first end, a main conduit extending towards the second end, and a plurality of process chambers distributed along the main conduit, wherein the main conduit is in fluid communication with the loading chamber and the plurality of process chambers; and
    a carrier attached to a first major side of the sample processing device, the carrier comprising a carrier body spaced from at least a portion of the first major side of the sample processing device, and the carrier further comprising a rail aligned with the main conduit on the sample processing device, wherein the carrier body is spaced from the sample processing device.

2. The assembly of claim 1, wherein the carrier comprises a plurality of carrier openings, the plurality of carrier openings aligned with the plurality of process chambers in the sample processing device.

3. The assembly of claim 1, wherein the sample processing device comprises first and second major sides attached with a layer of pressure sensitive adhesive, and wherein at least one of the main conduits is closed between the process chambers and the loading chamber by the pressure sensitive adhesive adhering to the first and second major sides together along the main conduit.

4. The assembly of claim 1, wherein the process chambers are elongated along an axis extending between the first and second opposing ends of the sample processing device.

5. The assembly of claim 1, wherein each of the process chambers is in fluid communication with the main conduit through a feeder conduit, and further wherein the feeder conduits form feeder conduit angles with the main conduit that are less than 90 degrees.

6. The assembly of claim 5, wherein the feeder conduits enter the process chambers proximate the first end of the device.

7. The assembly of claim 5, wherein each of the feeder conduits comprises a cross-sectional area that is smaller than the cross-sectional area of the main conduit.

8. The assembly of claim 1, wherein the loading chamber comprises a loading port and a vent port.

9. The assembly of claim 3, wherein the pressure sensitive adhesive comprises a silicone-based pressure sensitive adhesive.

10. A sample processing assembly comprising:
    a sample processing device comprising first and second opposing ends and a plurality of unvented process arrays, wherein each unvented process array comprises a loading chamber located proximate the first end, a main conduit extending towards the second end, and a plurality of process chambers distributed along the main conduit, wherein the main conduit is in fluid communication with the loading chamber and the plurality of process chambers; and a carrier attached to a first major side of the sample processing device, the carrier comprising a carrier body spaced from at least a portion of the first major side of the sample processing device, and the carrier further comprising a rail aligned with each of the main conduits on the sample processing device, wherein the carrier body is spaced from the sample processing device between adjacent main conduits.

11. The assembly of clam 10, wherein the carrier comprises a plurality of carrier openings, the plurality of carrier openings aligned with the plurality of process chambers in the sample processing device.

12. The assembly of claim 10, wherein the sample processing device comprises first and second major sides attached with a layer of pressure sensitive adhesive, and wherein at least one of the main conduits is closed between the process chambers and the loading chamber by the pressure sensitive adhesive adhering to the first and second major sides together along the main conduit.

13. The assembly of claim 10, wherein the process chambers are elongated along an axis extending between the first and second opposing ends of the sample processing device.

14. The assembly of claim 10, wherein each of the process chambers is in fluid communication with the main conduit through a feeder conduit, and further wherein the feeder conduits form feeder conduit angles with the main conduit that are less than 90 degrees.

15. The assembly of claim 14, wherein the feeder conduits enter the process chambers proximate the first end of the device.

16. The assembly of claim 14, wherein each of the feeder conduits comprises a cross-sectional area that is smaller than the cross-sectional area of the main conduit with which it is in fluid communication.

17. The assembly of claim 10, wherein each of the loading chambers comprises a loading port and a vent port.

18. The assembly of claim 12, wherein the pressure sensitive adhesive comprises a silicone-based pressure sensitive adhesive.

* * * * *